United States Patent [19]

Fayram et al.

[11] Patent Number: 5,658,321
[45] Date of Patent: Aug. 19, 1997

[54] CONDUCTIVE HOUSING FOR IMPLANTABLE CARDIAC DEVICE

[75] Inventors: Timothy A. Fayram, Gilroy; Eric S. Fain, Menlo Park, both of Calif.

[73] Assignee: Ventritex, Inc., Sunnyvale, Calif.

[21] Appl. No.: 489,096

[22] Filed: Jun. 9, 1995

[51] Int. Cl.$^6$ .................................................. A61N 1/39
[52] U.S. Cl. ................................................. 607/36
[58] Field of Search ................................... 607/5, 9, 36

[56] References Cited

U.S. PATENT DOCUMENTS

| | | | |
|---|---|---|---|
| 4,008,748 | 2/1977 | Schulman | 607/38 |
| 4,532,931 | 8/1985 | Mills | 128/419 |
| 4,558,702 | 12/1985 | Barreras et al. | 128/419 |
| 4,727,877 | 3/1988 | Kallok | 128/419 |
| 4,825,871 | 5/1989 | Cansell | 128/419 |
| 4,922,927 | 5/1990 | Fine et al. | 128/786 |
| 5,133,353 | 7/1992 | Hauser | 128/419 |
| 5,261,400 | 11/1993 | Bardy | 607/5 |
| 5,314,430 | 5/1994 | Bardy | 607/5 |
| 5,374,279 | 12/1994 | Duffin, Jr. et al. | 607/5 |
| 5,376,103 | 12/1994 | Anderson et al. | 607/5 |
| 5,385,574 | 1/1995 | Hauser et al. | 607/4 |
| 5,439,484 | 8/1995 | Mehra | 607/5 |

OTHER PUBLICATIONS

"Woven Wire Patches are Superior to Solid Disks for Subcutaneous Electrodes: Implications for Active Can Defibrillation", Leonelli, et al., PACE, vol. 18, Part II, Jan. 1995, pp. 225–228.

*Primary Examiner*—Lee S. Cohen
*Attorney, Agent, or Firm*—Steven M. Mitchell; Mark J. Meltzer

[57] ABSTRACT

An implantable cardiac stimulator having a housing defining an interior cavity and having an exterior surface, and a defibrillation pulse generator circuit contained within the cavity. The housing exterior surface has a number of ridges, and each ridge includes at least two surfaces that are angularly offset from each other at an edge. The ridges may be formed by creating grooves in the housing in a closely spaced arrangement.

17 Claims, 3 Drawing Sheets

FIG. 2
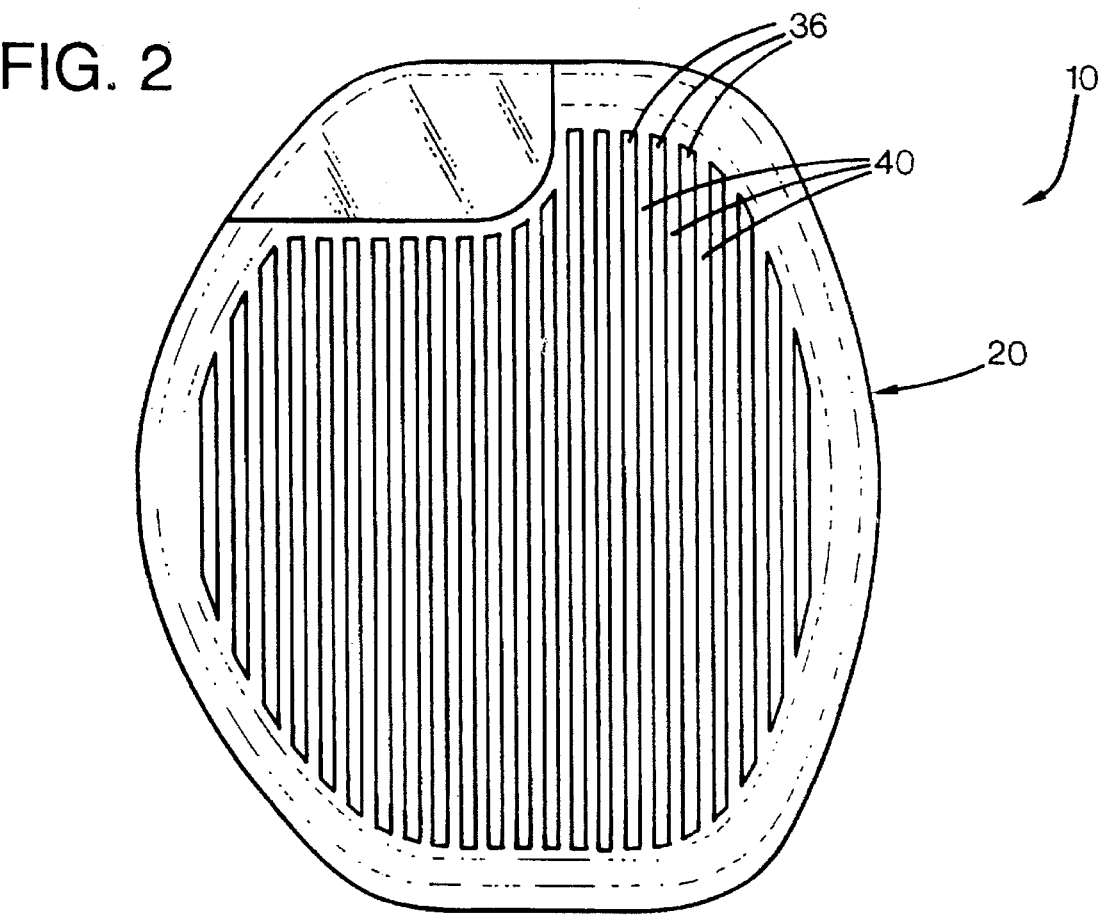
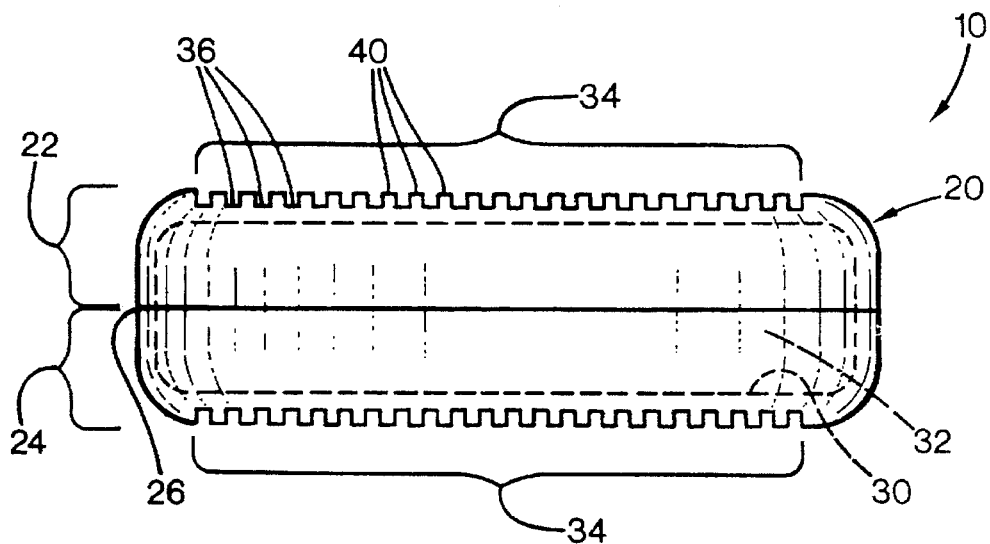
FIG. 3

CONDUCTIVE HOUSING FOR IMPLANTABLE CARDIAC DEVICE

FIELD OF THE INVENTION

The present invention relates generally to implantable cardiac stimulation devices, and more particularly to a defibrillation pulse generator having an electrically conductive housing used as an electrode.

BACKGROUND AND SUMMARY OF THE INVENTION

Defibrillators are implanted in patients susceptible to cardiac tachyarrhythmias including tachycardia or fibrillation. Such devices provide cardioversion or defibrillation by delivering a high voltage shock to the patient's heart, typically about 500–750 V. Current devices typically apply this voltage between two transvenously placed electrodes: one at the distal end of a lead inserted into the patient's right ventricle (RV), and the other in the superior vena cava (SVC) region. A third electrode which is typically electrically coupled to the second electrode may be a subcutaneous patch implanted in the area of the left chest wall, or may simply be provided by the metallic housing or "can" of a pectorally implanted defibrillator. When the housing of the defibrillator is used as an electrode, it is sometimes referred to as an "active can" device.

Active can defibrillators enjoy the primary advantage that they do not require the additional surgical procedure to implant the subcutaneous patch. However, active can defibrillators used with RV and SVC electrodes may require a higher defibrillation threshold voltage than electrode systems using an RV, SVC and subcutaneous patch electrode combination. This may result from the longer conduction path between the heart and a pectorally implanted housing, as compared to the shorter path from the heart to a patch implanted beneath the skin of the left lateral chest wall.

An existing approach to improve the performance of active can devices is to increase the effective surface area of the can by attaching a sheet of mesh woven of conductive round wire to the housing. Such a device is disclosed in U.S. Pat. No. 5,385,574 to Hauser, et al. This may provide some reduction in the resistance of the interface between the housing and the surrounding tissue.

The disclosed embodiment provides an improved active can defibrillator by providing an implantable cardiac stimulator having a housing defining an interior cavity and having an exterior surface, and a defibrillation pulse generator circuit contained within the cavity. The housing exterior surface has a number of ridges. Each ridge may include at least two surfaces that are angularly offset from each other at an edge to form a sharp external corner. The ridges may be formed by creating grooves in the housing in a closely spaced arrangement.

BRIEF DESCRIPTION OF THE DRAWINGS

FIG. 2 is a plan view of the embodiment of FIG. 1.

FIG. 3 is a side view of the embodiment of FIG. 1.

DETAILED DESCRIPTION OF A PREFERRED EMBODIMENT

Figure 1:
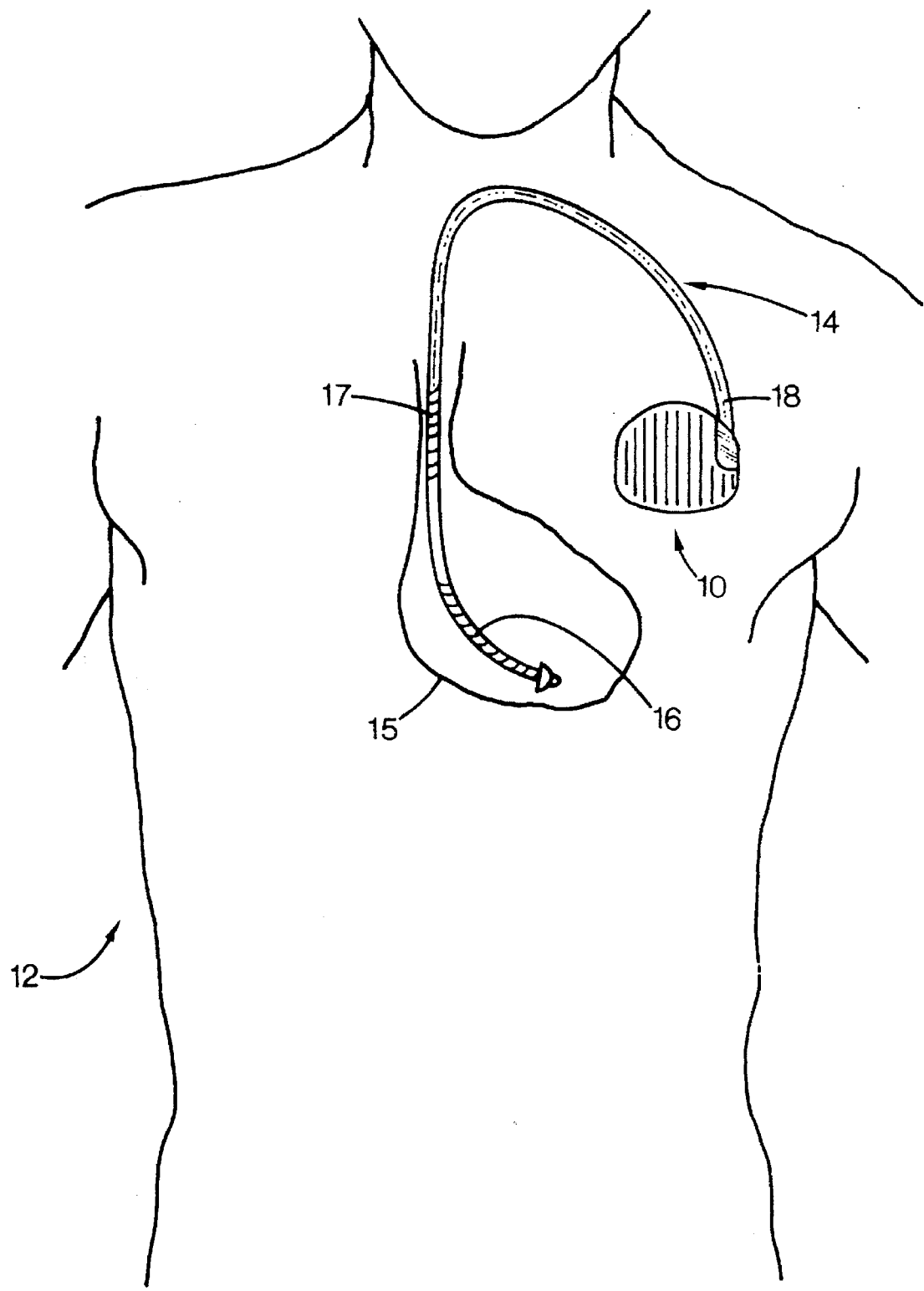
FIG. 1 is an overview of a preferred embodiment of the invention as implanted in a patient.

FIG. 1 illustrates an implantable defibrillator or pulse generator 10 according to the present invention as pectorally implanted in a patient 12. It may have bradycardia and antitachycardia pacing capabilities as well as cardioversion and defibrillation capabilities. A sensing/pacing and defibrillation lead 14 extends from the defibrillator 10 to the patient's heart 15. The lead has an RV defibrillation electrode 16 at the distal end for placement within the heart, an SVC defibrillation electrode 17 on the lead body for placement in the SVC region, and a proximal end 18 having multiple end portions each containing one or more conductors and terminating in a connector attachable to the defibrillator.

As shown in FIGS. 2 and 3, the defibrillator 10 includes a housing 20 formed of a corrosion resistant biocompatible metal such as titanium, with numerous electronic components including a defibrillation pulse generator circuit (not shown) contained within the housing. The housing is electrically connected to the high voltage output of the pulse generator circuit so that it may serve as an electrode. Thus, a defibrillation shock is applied as a voltage difference between the housing and the RV electrode 16, and if an SVC electrode is used is connected with that electrode.

As shown in FIG. 3, the housing is formed of two similar dish shaped halves 22, 24, joined at their rims at a seam 26 that may be laser welded for hermeticity. The halves have interior surfaces 30 that define a cavity 32. Each housing half 22, 24 has a major generally flat exterior surface portion 34 that is contoured or textured to provide decreased electrical resistance between the housing and the surrounding tissue. Alternatively, the housing may have a somewhat concave or convex profile. In a first preferred embodiment, the housing is patterned with an array of parallel rectangular grooves 36. The grooves alternate with an array of ridges 40, each of which stands between and defines adjacent grooves. This pattern is produced by machining the grooves into the smooth surface of the housing.

Figure 4:
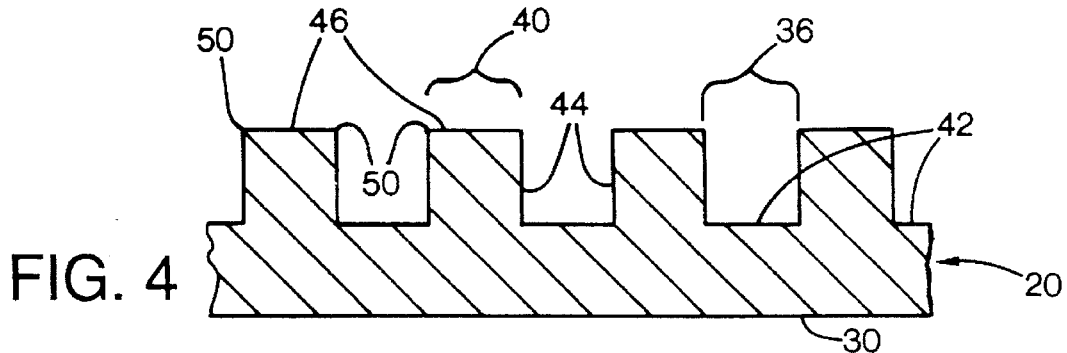
FIG. 4 is an enlarged sectional side view of the embodiment of FIG. 1.

As shown in FIG. 4, each groove 36 is a rectangular channel having a floor 42 and parallel opposed side walls 44 facing each other. Each of the ridges 40 has a rectangular profile, with a flat top or original surface 46 at a level above the floors 42. The side walls 44 meet the top surface of each ridge at a sharp corner edge 50. Preferably, this corner has no radius, or a very small radius of less than 0.02 mm.

The increased surface area of the articulated surface portions 34 provides reduced electrical resistance at the housing/tissue interface. In addition, the sharp corners joining the many facets have been found to contribute an further resistance reduction. This is believed to be caused at least in part by the tendency of similarly charged particles such as electrons to repel. The applied voltage for a defibrillation shock creates a concentration of electrons at the surfaces of the housing. Consequently, those electrons on a flat surface portion near a protruding corner will tend to be electrostatically repelled by the adjacent electrons, with the repulsion pushing those electrons in a direction beyond the corner and into the adjoining tissue.

Essentially, an electron at the corner of a ridge is acted on by the primary voltage force vector diagonally into the tissue. In addition, the build up of electrons along the top surface generates an electrostatic force vector laterally into the tissue, while the build up of electrons along the side wall surface generates an electrostatic force vector perpendicularly into the tissue. The sum of the electrostatic force vectors is in the same diagonal direction as the primary voltage force vector, yielding a greater total force on the electrons near the corner. This mechanism by which electrons "leak" out of the corners is believed to be the cause of the reduction in the effective resistance of the interface that has been experimentally observed.

Each housing half of the embodiment of FIG. 4 is preferably stamped and formed into the dish shape from a sheet of titanium with a series of progressive dies. The formed half is then placed over a core that closely fits within the cavity so that the interior surface 30 rests securely against the core. A numerically controlled milling machine may then cut the grooves with an end mill of less than or equal to the width of the grooves. An alternative machining method uses a narrow saw blade traveling in a continuous loop to cut the rectangular groove. The housing must be indexed relative to the saw blade for each parallel groove. The sharp edges left by the machining process are preferably maintained in their sharp condition, without using any abrasive, chemical, or mechanical process that might otherwise be used to radius or deburr the edges.

In the preferred embodiment, the housing has a height of 73 mm, a width of 65 mm, a thickness of 12.7 mm, and an overall wall thickness of 0.50 mm between the inner surface 30 and the top surfaces 46. The grooves are cut to a depth of 0.25 mm and a width of 0.40 mm, with a pitch of 0.80 mm providing a ridge width of 0.40 mm. The housing perimeter has a radius of 3.56 mm, with the grooves being cut to a constant depth so that they terminate by passing off the edge of the housing face as the radius curves away at the perimeter.

The groove and ridge dimensions may vary widely while retaining the benefits of the invention. For structural soundness and manufacturing convenience, it is preferred that the groove width be about 50% of the pitch, although a range of 20–80% is believed to be effective without creating ridges that are too fragile or grooves that are too narrow to readily machine. Using electron discharge machining (EDM), it is believed possible to generate groove and ridge widths of 0.001 inch (0.025 mm) or larger. Other methods may provide smaller features that function effectively. The machined grooves and ridges may be as large as 3.0 mm or more, although conductivity effects of the invention are diminished as the number of ridges decreases. The grooves may be as deep as the wall thickness of the housing permits, up to 3.0 mm or more, and may be a small fraction of the groove width to provide a shallow having a depth as small as 0.001 inch (0.025 mm).

Figure 5:
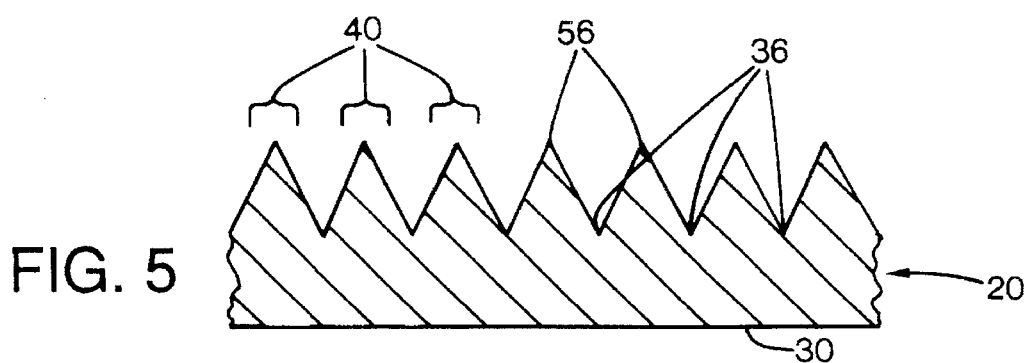
FIG. 5 is an enlarged sectional side view of a first alternative embodiment of the invention.
Figure 6:
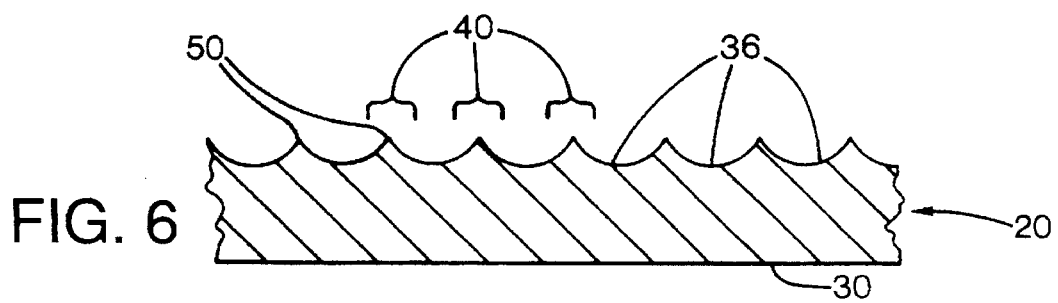
FIG. 6 is an enlarged sectional side view of a second alternative embodiment of the invention.

FIGS. 5 and 6 show alternative patterns that may be formed on the housing exterior with sharp edges or corners to provide reduced electrical resistance. In FIG. 5, a saw tooth pattern having an array of parallel elongated peaked ridges provides the beneficial sharp edges. While the peaks form somewhat acute angles, it is not critical for the angles at the recesses of the grooves to be sharp. FIG. 6 shows a scalloped surface in which the peaks are sharp, but the valleys are gently curved. This embodiment does not provide as significant of a surface area advantage as the preferred embodiment, but may be useful where there is a concern about contaminants being trapped in sharp recesses.

The alternative embodiments may be manufactured with grooves on a much smaller scale than in the preferred embodiment. FIGS. 5 and 6 may be produced by a machining process in which a sharp pointed tool is swept over the surfaces repeatedly as the housing is moved, with each groove being formed on a single pass. Circular or spiral patterns of concentric arcuate grooves may also be formed, such as by "facing" the housing on a numerically controlled milling machine. A carbide tool may be used to form small grooves that define sharp peaks. Alternatively, an electron discharge machining process may be used to generate smaller features having sharp external corners. It is believed to be possible to form a textured surface having ridges with a spacing on the order of an optical reflection grating to achieve at least some of the benefits of the invention. Alternatively, an irregular surface may be formed by grinding, abrading, brushing, or chemically etching the surface to generate sharp peaks, which may be elongated ridges or individual pointed peaks.

Figure 7:
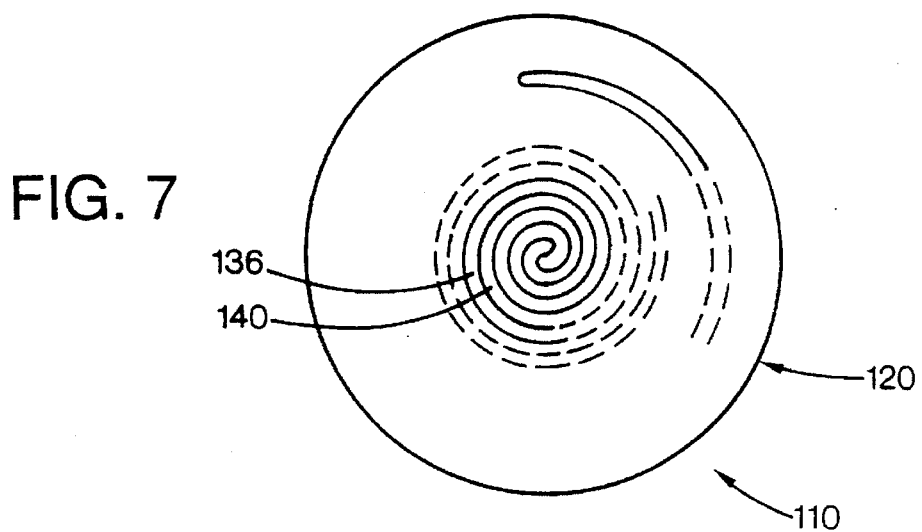
FIG. 7 is a schematic plan view of a fourth alternative embodiment of the invention.

A further alternative embodiment is shown in FIG. 7. A defibrillator 110 has a housing 120 defining a spiral groove 136 (not shown to scale). The groove is defined by a corresponding ridge 140. In this embodiment, a sawtooth groove has a 90 degree V-shaped cross section, with a groove width and depth of 0.13 mm, and a ridge width of 0.25 mm. The spiral groove may be formed by a pointed countersink tool in the manner discussed above with respect to FIG. 4, or as shown in FIG. 5. Although circular grooves may be machined as an alternative, the spiral groove speeds machining by avoiding the need for plunging and withdrawing the tool to form each circular groove. The patterns of FIGS. 4, 5, and 6 may all be generated in either a spiral or concentric arrangement.

Another embodiment of the invention covers a portion of the housing 20 with a thin coating (not shown) of an insulator such as Parylene or silicone rubber. This provides an improved directionality for the defibrillation current. The coating exhibits improved adhesion to the housing surface where the surface is textured. This is particularly beneficial at the edges of the insulation.

While the invention is described in terms of preferred and alternative embodiments, the following claims are not intended to be so limited.

We claim:

1. An implantable cardiac stimulator comprising:

a housing defining an interior cavity and having an exterior surface;

a defibrillation pulse generator circuit contained within the cavity; and the housing exterior surface including at least a first portion having a multitude of ridges.

2. The implantable cardiac stimulator of claim 1 wherein each ridge includes at least two surfaces that are angularly offset from each other at an edge.

3. The implantable cardiac stimulator of claim 2 wherein the edge of each ridge is a corner having a radius of between 0 and 0.20 mm.

4. The implantable cardiac stimulator of claim 2 wherein the edge of each ridge is a sharp corner without a radius.

5. The implantable cardiac stimulator of claim 1 wherein the first portion of the exterior surface defines recessed grooves between the ridges.

6. The implantable cardiac stimulator of claim 5 wherein each recessed groove has opposed side walls facing each other.

7. The implantable cardiac stimulator of claim 5 wherein each ridge includes an original exterior surface portion comprising the top of the ridge, and opposed first and second side walls comprising the sides of the ridge, such that each ridge includes two edges, each defined at the junction between one of the side walls and the top of the ridge.

8. The implantable cardiac stimulator of claim 5 wherein the grooves have a depth of between 0.025 and 3.0 mm.

9. The implantable cardiac stimulator of claim 1 wherein the housing is formed of titanium.

10. The implantable cardiac stimulator of claim 1 wherein the first portion includes an array of closely spaced parallel ridges.

11. The implantable cardiac stimulator of claim 1 wherein the first portion includes an array of closely spaced substantially concentric arcuate ridges.

12. The implantable cardiac stimulator of claim 11 wherein the ridges comprise a spiral shape.

13. The implantable cardiac stimulator of claim 1 and further including an insulative coating covering a portion of the housing exterior surface.

14. A housing for an implantable cardiac stimulator comprising:

a housing body defining an interior cavity for receiving a defibrillation pulse generator circuit;

the housing having an exterior surface;

the housing exterior surface including at least a first portion having a multitude of ridges; and each ridge including at least two surfaces that are angularly offset from each other at an edge.

15. The housing of claim 14 wherein the first portion of the exterior surface defines a plurality of recessed grooves, each defined between adjacent ridges.

16. The housing of claim 14 wherein the edge is a sharp corner without a radius.

17. The housing of claim 14 wherein the first portion includes an array of closely spaced ridges.

* * * * *